United States Patent
Kuroda (10) Patent No.: US 8,476,073 B2
(45) Date of Patent: Jul. 2, 2013

(54) AUTOMATIC ANALYZING APPARATUS AND QUALITY CONTROL METHOD FOR ANALYSIS SUPPORTING LIQUID IN THE SAME

(75) Inventor: Akihisa Kuroda, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 325 days.

(21) Appl. No.: 12/248,444

(22) Filed: Oct. 9, 2008

(65) Prior Publication Data

US 2009/0087914 A1 Apr. 2, 2009

Related U.S. Application Data

(63) Continuation of application No. PCT/JP2007/058067, filed on Apr. 12, 2007.

(30) Foreign Application Priority Data

Apr. 12, 2006 (JP) .................................. 2006-109719

(51) Int. Cl.
*G01N 35/02* (2006.01)
(52) U.S. Cl.
USPC ............... 436/50; 436/164; 436/165; 422/62; 422/67; 422/82.05; 422/3; 700/266
(58) Field of Classification Search
USPC ........... 422/3, 62, 67, 50, 55, 56, 68.1, 82.05; 436/50, 164, 165, 805; 700/266, 78, 79, 80; 702/182, 183, 185
See application file for complete search history.

(56) References Cited

U.S. PATENT DOCUMENTS

| | | | |
|---|---|---|---|
| 4,276,051 A | 6/1981 | Ginsberg et al. | |
| 2004/0219063 A1* | 11/2004 | Heiner et al. | 422/68.1 |

FOREIGN PATENT DOCUMENTS

| | | |
|---|---|---|
| JP | 56-119853 | 9/1981 |
| JP | 03-110475 | 5/1991 |
| JP | 04-329358 | 11/1992 |
| JP | 06-265555 | 9/1994 |
| JP | 11-94839 A | 4/1999 |
| JP | H11-094843 | 4/1999 |
| JP | 2001-264283 | 9/2001 |

OTHER PUBLICATIONS

Japanese Office Action for Application No. JP 2006-109719, dated Jul. 4, 2011, 3 pages.

* cited by examiner

*Primary Examiner* — Jyoti Nagpaul
(74) *Attorney, Agent, or Firm* — Kilpatrick Townsend & Stockton LLP (57) ABSTRACT

An automatic analyzing apparatus can properly determine a quality of an analysis supporting liquid, after being supplied to the automatic analyzing apparatus, which supports an analysis performed in the automatic analyzing apparatus and can properly maintain an accuracy of the analysis. The analysis supporting liquid which supports an analysis of a specimen is dispensed into a reaction vessel by using a specimen dispensing unit which dispenses the specimen, a reagent dispensing unit which dispenses a reagent, a cleaning unit which cleans the reaction vessel, or a diluted solution dispensing unit which dispenses a diluted solution. An optical measurement is performed with respect to a liquid including the dispensed analysis supporting liquid in the reaction vessel. Analysis data of the analysis supporting liquid is generated by using the measured result. The quality of the analysis supporting liquid is determined by comparing the generated analysis data with reference data.

7 Claims, 4 Drawing Sheets

AUTOMATIC ANALYZING APPARATUS AND QUALITY CONTROL METHOD FOR ANALYSIS SUPPORTING LIQUID IN THE SAME

CROSS-REFERENCE TO RELATED APPLICATIONS

This application is a continuation of PCT international application Ser. No. PCT/JP2007/058067 filed on Apr. 12, 2007 which designates the United States, incorporated herein by reference, and which claims the benefit of priority from Japanese Patent Application No. 2006-109719, filed on Apr. 12, 2006, incorporated herein by reference.

BACKGROUND OF THE INVENTION

1. Field of the Invention

The present invention relates to an automatic analyzing apparatus which causes a specimen and a reagent to react to perform an analysis on the specimen, and performs a quality control of an analysis supporting liquid as a liquid for supporting the analysis on the specimen; and a quality control method for the analysis supporting liquid in the automatic analyzing apparatus.

2. Description of the Related Art

In an automatic analyzing apparatus which causes a specimen and a reagent to react to perform an analysis on the specimen, purified water such as ion exchanged water and distilled water has been widely used at least as a part of an analysis supporting liquid such as a pressure transmitting medium, a cleaning liquid for a reaction vessel, and a diluted solution in a dispensing mechanism which dispenses the specimen or the reagent (see Japanese Patent Application Laid-Open No. H11-94843, for example). Such purified water is supplied from a purified water device to the automatic analyzing apparatus via a duct system and accumulated in a purified water tank in the automatic analyzing apparatus.

A quality control of the purified water essential to the analysis is important in an enhancement of a reliability of the automatic analyzing apparatus. Therefore, the quality control of the purified water has conventionally been performed by providing a water purity meter in a vicinity of an outlet of the purified water device and measuring a specific resistance value (or a specific electric conductivity) of the purified water having passed through the water purity meter.

SUMMARY OF THE INVENTION

A quality control method according to an aspect of the present invention is for an analysis supporting liquid in an automatic analyzing apparatus which includes, to perform an analysis on a specimen, a specimen dispensing unit which dispenses the specimen by using, as a pressure transmitting medium, an analysis supporting liquid including purified water and serving to support the analysis on the specimen, a reagent dispensing unit which dispenses a reagent by using the analysis supporting liquid as the pressure transmitting medium, a cleaning unit which cleans, by using the analysis supporting liquid as a cleaning liquid, a reaction vessel in which the specimen and the reagent are mixed and made react to each other, and a diluted solution dispensing unit which dispenses a diluted solution including the analysis supporting liquid, and which controls a quality of the analysis supporting liquid. The quality control method includes dispensing the analysis supporting liquid into the reaction vessel by one of the specimen dispensing unit, the reagent dispensing unit, the cleaning unit, and the diluted solution dispensing unit; performing an optical measurement with respect to a liquid, including the analysis supporting liquid dispensed in the dispensing, in the reaction vessel; generating analysis data of the analysis supporting liquid by using a result measured in the performing the optical measurement; and determining the quality of the analysis supporting liquid by comparing the analysis data generated in the data generating with reference data.

An automatic analyzing apparatus according to another aspect of the present invention includes a specimen dispensing unit which dispenses a specimen by using, as a pressure transmitting medium, an analysis supporting liquid including purified water and serving to support an analysis on the specimen; a reagent dispensing unit which dispenses a reagent by using the analysis supporting liquid as the pressure transmitting medium; a cleaning unit which cleans, by using the analysis supporting liquid as a cleaning liquid, a reaction vessel in which the specimen and the reagent are mixed and made react to each other; a diluted solution dispensing unit which dispenses a diluted solution including the analysis supporting liquid; a photometric unit which performs an optical measurement with respect to a liquid including the analysis supporting liquid dispensed into the reaction vessel by one of the specimen dispensing unit, the reagent dispensing unit, the cleaning unit, and the diluted solution dispensing unit; a data generating unit which uses a result measured by the photometric unit to generate analysis data of the analysis supporting liquid; and a quality determining unit which compares the analysis data generated by the data generating unit with reference data to determine a quality of the analysis supporting liquid.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention (hereinafter referred to as "embodiments") will be explained below with reference to the accompanying drawings.

The wording "purified water" in the description indicates ion exchanged water, water purified by a reverse osmosis membrane, distilled water, refined water, and the like which can be used as the analysis supporting liquid. The "liquid" in the present invention indicates a liquid which contains a small amount of solid ingredient.

Figure 1:
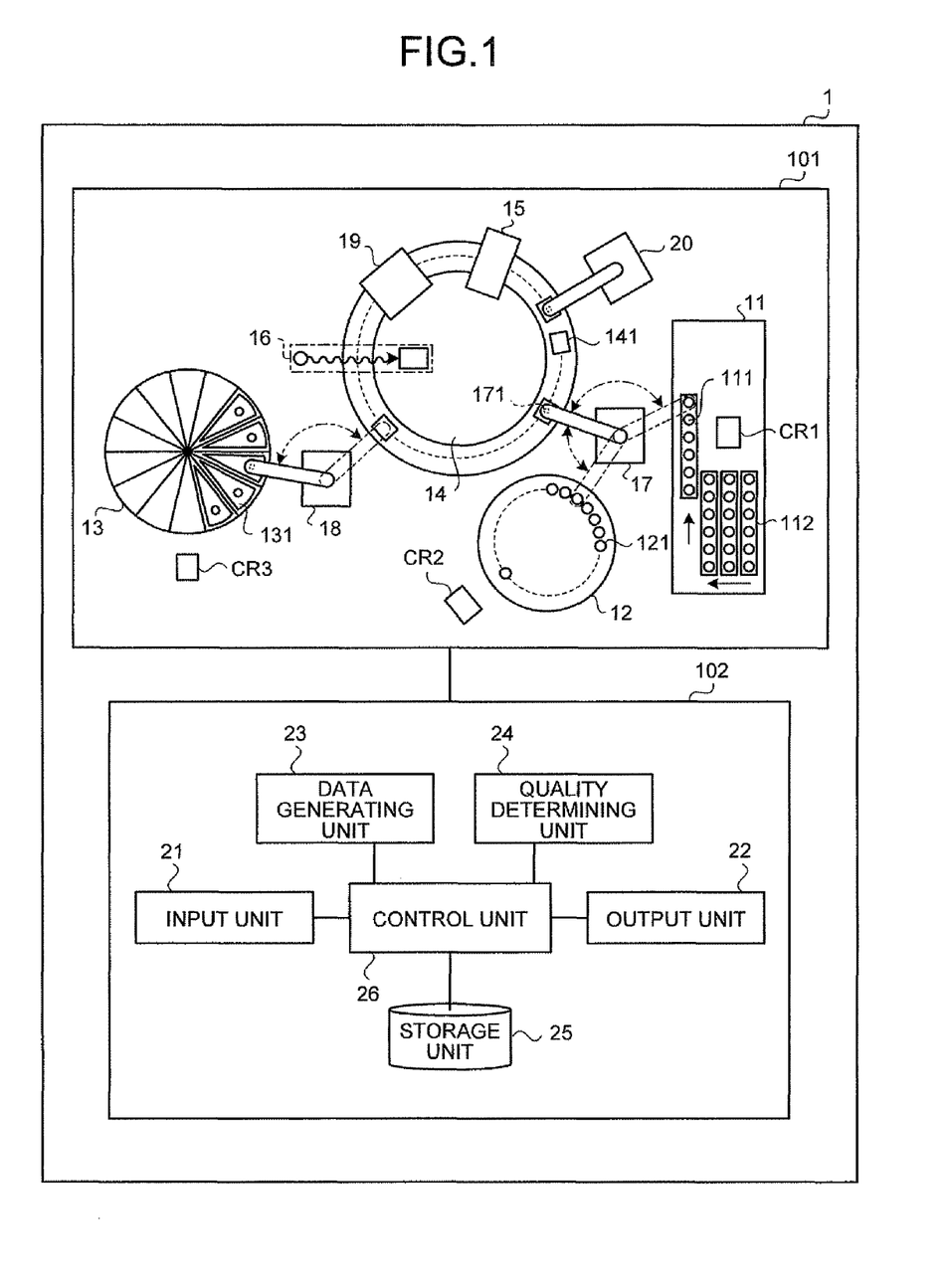
FIG. 1 schematically shows a structure of a substantial part of an automatic analyzing apparatus according to an embodiment of the present invention.

FIG. 1 schematically shows a structure of a substantial part of an automatic analyzing apparatus according to an embodiment of the present invention. An automatic analyzing apparatus 1 shown in FIG. 1 includes a measuring mechanism 101 which dispenses a specimen and a reagent respectively into predetermined vessels and performs an optical measurement with respect to a liquid in each vessel; and a controlling/analyzing mechanism 102 which performs a control of the automatic analyzing apparatus 1 including the measuring mechanism 101 and performs an analysis on a measurement result in the measuring mechanism 101, as an apparatus which automatically and continuously performs a biochemical analysis on a plurality of specimens through a cooperation of the two mechanisms. It should be noted that the "liquid" described here includes a liquid containing a small amount of solid ingredient.

First, the measuring mechanism 101 of the automatic analyzing apparatus 1 will be explained. The measuring mechanism 101 includes a specimen transporting section 11 which stores and sequentially transports a plurality of racks 112 which have a specimen vessel 111 mainly housing a general specimen; a specimen vessel retainer 12 which retains a specimen vessel 121 housing a specimen of various types (a standard specimen for generating a calibration curve, a specimen for accuracy control, an emergency specimen, a STAT specimen, a specimen for a retest, and the like) other than the general specimen; a reagent vessel retainer 13 which retains a reagent vessel 131; a reaction vessel retainer 14 which retains a reaction vessel 141 as a vessel which causes the specimen (specimen) and the reagent to react; a stirring unit 15 which stirs the liquid housed in the reaction vessel 141; and a photometric unit 16 which measures an intensity and the like of each wavelength component of a light having passed through an inside of the reaction vessel 141.

The measuring mechanism 101 further includes a specimen dispensing unit 17 which dispenses, into the reaction vessel 141, the specimen such as the specimen housed in the specimen vessel 111 provided on the specimen transporting section 11 and in the specimen vessel 121 provided on the specimen vessel retainer 12; a reagent dispensing unit 18 which dispenses the reagent housed in the reagent vessel 131 provided on the reagent vessel retainer 13 into the reaction vessel 141; a cleaning unit 19 which cleans the reaction vessel 141; and a diluted solution dispensing unit 20 which dispenses a diluted solution that dilutes the liquid in the reaction vessel 141.

An information code recording medium (not shown) which records identifying information for identifying each housed-in specimen via an encoding into an information code such as a bar code, a two-dimensional code, or the like is affixed to each of the specimen vessels 111 and 121. Similarly, an information code recording medium (not shown) which records identifying information for identifying a housed-in reagent via the encoding into the information code is affixed to the reagent vessel 131. Consequently, the measuring mechanism 101 is provided with an information code reader CR1 which reads out the information code affixed to the specimen vessel 111, an information code reader CR2 which reads out the information code affixed to the specimen vessel 121, and an information code reader CR3 which reads out the information code affixed to the reagent vessel 131.

Each of the specimen vessel retainer 12, the reagent vessel retainer 13, and the reaction vessel retainer 14 includes a wheel (not shown) which houses and retains each of the specimen vessel 121, the reagent vessel 131, and the reaction vessel 141; and a driving unit (not shown) which is attached at a center of a bottom surface of the wheel and axially rotates the wheel by a vertical line, as a rotation axis, passing through the center.

An inside of each vessel retainer is kept at a constant temperature. For example, a temperature of an inside of the reagent vessel retainer 13 is set to be lower than an ambient temperature to suppress a deterioration and a denaturation of the reagent. Besides, a temperature of an inside of the reaction vessel retainer 14 is set to be as high as the human body temperature.

The photometric unit 16 includes a light source which emits a white light; a spectroscopic optical system which disperses the white light having passed through the reaction vessel 141; and a light receiving element which receives each component of the light dispersed in the spectroscopic optical system and converts into an electric signal.

Figure 2:
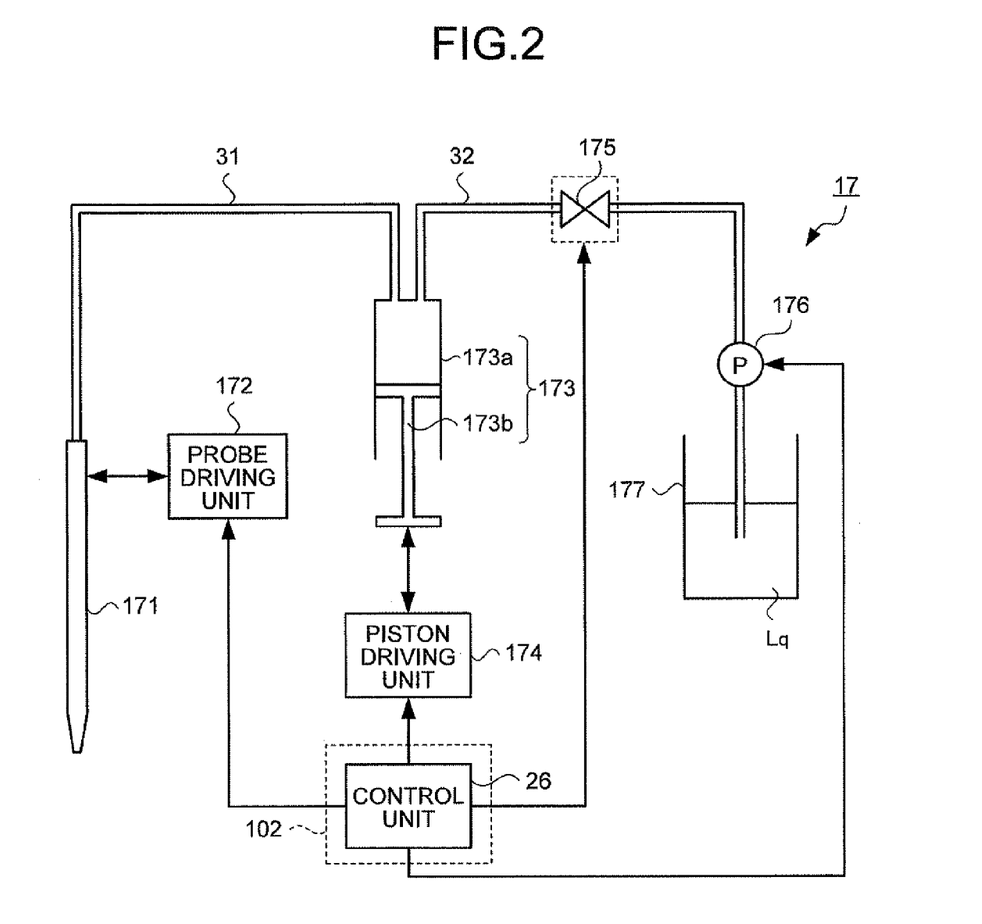
FIG. 2 schematically shows a structure of a specimen dispensing unit.

FIG. 2 schematically shows a structure of the specimen dispensing unit 17. The specimen dispensing unit 17 shown in FIG. 2 includes a hollow probe 171 having a tapered tip end for absorbing and discharging the specimen; a probe driving unit 172 having an arm and the like which moves up and down the probe 171 in the vertical direction and makes the probe 171 swing in the horizontal direction; a tube 31 (a part of the duct system) constituting a flow path of a cleaning liquid Lq which supports, as a pressure transmitting medium for transmitting a pressure to the probe 171, the absorption and the discharge of the specimen by the probe 171; and a syringe 173 which generates the pressure to be applied to the probe 171 for absorbing or discharging the specimen via the cleaning liquid Lq in the tube 31.

The syringe 173 includes a cylinder 173a and a piston 173b, and the piston 173b slides and shifts inside the cylinder 173a by a piston driving unit 174, so that the pressure to be applied to the cleaning liquid Lq in the cylinder 173a is changed.

The syringe 173 is connected to a tube 32 constituting a part of the duct system as another flow path of the cleaning liquid Lq. An electromagnetic valve 175 which controls a flow of the cleaning liquid Lq and a pump 176 which performs the absorbing/discharging operation of the cleaning liquid Lq are sequentially interposed in the tube 32. An end of the tube 32 different from the other end connected to the syringe 173 reaches an inside of a cleaning liquid tank 177 which houses the cleaning liquid Lq.

For the cleaning liquid Lq as the analysis supporting liquid, purified water such as ion exchanged water, water purified by a reverse osmosis membrane, distilled water, or refined water is applicable. Such purified water is generated by a purified water device provided at an outside of the automatic analyzing apparatus 1, and supplied to the cleaning liquid tank 177 via a given duct system (the purified water device and the duct system being not shown though).

Operations including the movement of the probe 171, and the absorption and the discharge of the specimen in the probe 171 in the specimen dispensing unit 17 having the structure described above are controlled by a control unit 26 provided in the controlling/analyzing mechanism 102.

The reagent dispensing unit 18 has the same structure as the specimen dispensing unit 17. A structure of a part for discharging the cleaning liquid Lq in the cleaning unit 19 is also the same as that in the specimen dispensing unit 17. Besides, the diluted solution dispensing unit 20 has the same structure as the specimen dispensing unit 17 (the probe driving unit in this case may not include the swing function in the horizontal direction, though), and discharges the cleaning liquid Lq as a diluted solution into the reaction vessel 141. In the embodiment, all of the cleaning liquid Lq used in the reagent dispensing unit 18, the cleaning unit 19, and the diluted solution dispensing unit 20 is supplied from the cleaning liquid tank 177.

In performing a biochemical analysis, since two types of reagents are often used for one specimen, a reagent vessel retainer 13 for a first reagent and another reagent vessel retainer 13 for a second reagent may be separately provided. In this case, it is only necessary to provide two reagent dispensing units 18 respectively for the reagent vessel retainers 13. More generally, the reagent vessel retainer 13 and the reagent dispensing unit 18 can be provided in plural number.

In addition, the stirring unit 15 may be provided in plural number so that liquid in a plurality of reaction vessels 141 is simultaneously stirred at an appropriate timing after the dispense of the specimen, the reagent, or the diluted solution.

FIG. 1 is present with a main aim of schematically showing principal components of the measuring mechanism 101, and therefore a positional relationship among the components is not necessarily accurate. An accurate positional relationship among the components attributes to a design particular to be determined depending on various conditions including the number of reagent vessel retainers 13 and a rotation mode of the wheel of the reaction vessel retainer 14 during an interval of the dispensing operation.

Next, the controlling/analyzing mechanism 102 of the automatic analyzing apparatus 1 will be explained continuously with reference to FIG. 1. The controlling/analyzing mechanism 102 includes an input unit 21 which accepts an input of information necessary for the analysis of the specimen and information including an operation instructing signal for instructing an operation of the automatic analyzing apparatus 1; an output unit 22 which outputs information concerning the analysis of the specimen; a data generating unit 23 which generates analysis data of the specimen based on the measurement result in the measuring mechanism 101; a quality determining unit 24 which determines the quality of the analysis supporting liquid by using the analysis data generated by the data generating unit 23; a storage unit 25 which stores various types of information including the information concerning the analysis of the specimen and concerning the automatic analyzing apparatus 1; and a control unit 26 which performs a control of each function or each unit in the controlling/analyzing mechanism 102 and a driving control of the measuring mechanism 101.

The input unit 21 includes a keyboard and a mouse. Besides, a pointing device such as a trackball and a trackpad, and a user interface such as a microphone for an audio input may further be provided as the input unit 21.

The output unit 22 includes a display device such as a liquid crystal display, a plasma display, an organic EL display, and a CRT display, which displays various types of information. Besides, a speaker for an output and a printer which outputs information by printing on paper may further be provided as the output unit 22.

The data generating unit 23 performs an analyzing calculation of the measurement result received from the photometric unit 16 of the measuring mechanism 101. In this analyzing calculation, analysis data for each specimen is generated by calculating an absorbance of the liquid in the reaction vessel 141 based on the measurement result transmitted from the photometric unit 16 and performing an ingredient amount calculating processing and the like which uses the result of the absorbance calculation and various information such as a calibration curve and analysis parameters to quantitatively calculates an ingredient in the liquid in the reaction vessel 141. The analysis data generated in this manner is output from the output unit 22, and at the same time written and stored in the storage unit 25.

The quality determining unit 24 compares the analysis data generated by the data generating unit 23 with reference data stored in the storage unit 25 to determine the quality of the cleaning liquid Lq.

The storage unit 25 is realized by using a hard disk which magnetically stores various information and a memory which, when the automatic analyzing apparatus 1 executes a processing, loads from the hard disk and electrically stores a program of the processing, and stores and manages an analysis item, specimen information, a kind of specimen, a dispensing amount of the specimen and the reagent, an expiration date of the specimen and the reagent, information concerning the calibration curve used for the analysis, an expiration date of the calibration curve, parameters such as a reference value and a tolerance of each analysis item, necessary for the analysis, the analysis data generated by the data generating unit 23, and the like.

The program stored in the storage unit 25 includes a program which causes the automatic analyzing apparatus 1 to execute a quality control method (to be described later) for the analysis supporting liquid in the automatic analyzing apparatus according to the embodiment. The storage unit 25 may be provided with an auxiliary storage device which reads out information recorded in a recording medium such as a flexible disk, a CD-ROM, a DVD-ROM, and a flash memory, which can be read out by a computer, and the program described above can be recorded in such a recording medium.

The control unit 26 is realized by a CPU (Central Processing Unit) having a controlling function and a calculating function, and executes a calculation and a control of various types of operations of the automatic analyzing apparatus 1 by reading out the program stored in the storage unit 25 from the storage unit 25.

The controlling/analyzing mechanism 102 having the functional structure described above is realized by using one computer or a plurality of computers. When the controlling/analyzing mechanism 102 is realized by using a plurality of computers, it is only necessary to decentralize functions of the controlling/analyzing mechanism 102 arbitrarily to different computers, and to connect the computers directly to each other or by way of a communication network (the Internet, an intranet, a leased line network, a local area network, a telephone network, and the like) to each other.

Figure 3:
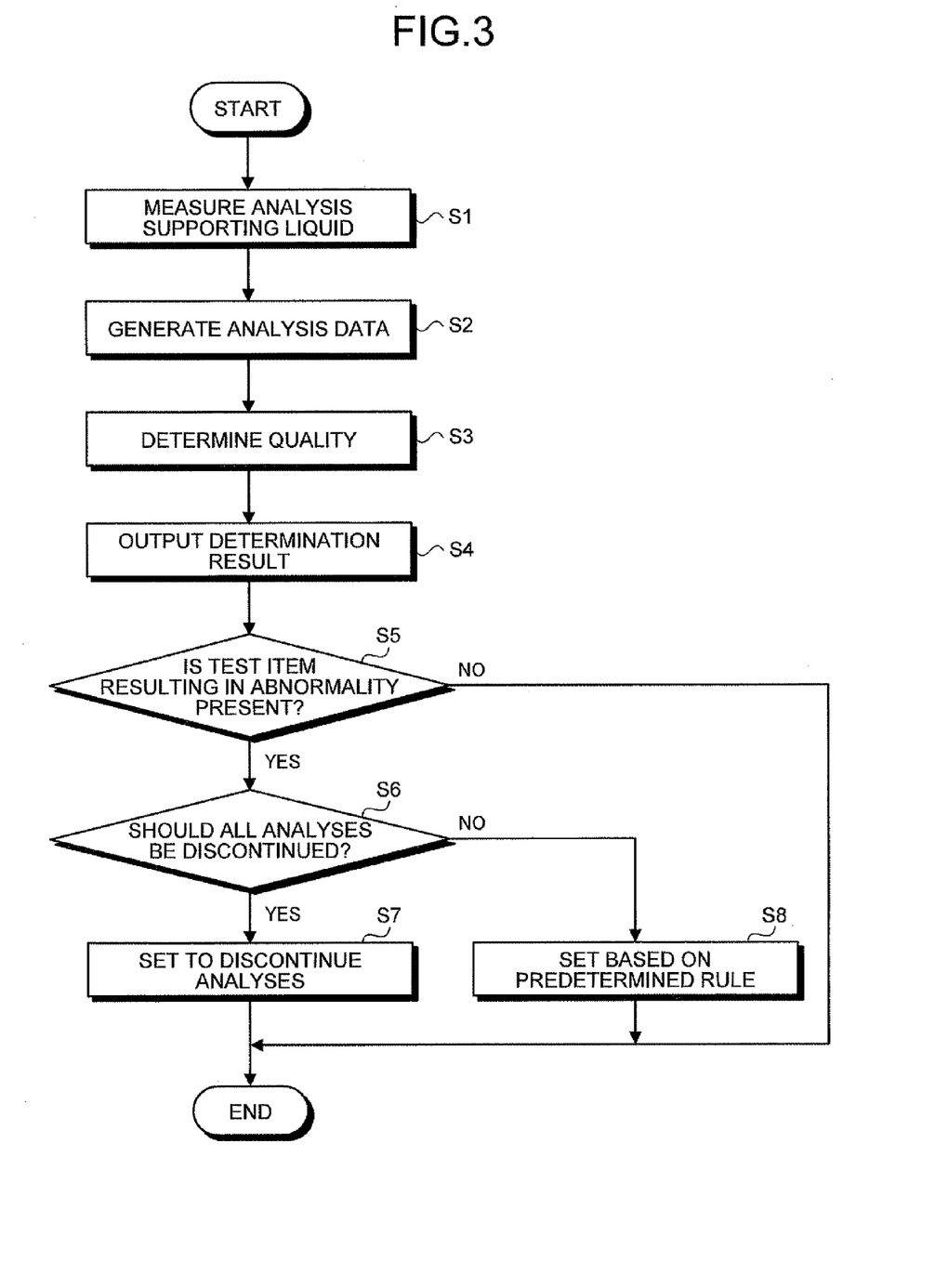
FIG. 3 is a flow chart showing an outline of a quality control method for an analysis supporting liquid in the automatic analyzing apparatus according to the embodiment of the present invention.

Next, a summary of a processing in the quality control method for the analysis supporting liquid in the automatic analyzing apparatus according to the embodiment will be explained with reference to a flow chart shown in FIG. 3. It should be noted that though the following explanation is given assuming the automatic analyzing apparatus 1 executes the processing, a structure of an automatic analyzing apparatus which performs the quality control method for the analysis supporting liquid according to the embodiment is not limited to that described above.

First, a measurement is performed by using, as a specimen, the cleaning liquid Lq which is the analysis supporting liquid (step S1). Specifically, the cleaning liquid Lq and the reagent are dispensed into the reaction vessel 141 and the photometric unit 16 performs an optical measurement with respect to the dispensed liquid (liquid mixture of the cleaning liquid Lq and the reagent) in the reaction vessel 141. The measurement by the photometric unit 16 here is performed during a rotation of the reaction vessel retainer 14.

The cleaning liquid Lq to be dispensed at step S1 is filled in a probe of any one of the specimen dispensing unit 17, the reagent dispensing unit 18, the cleaning unit 19, and the diluted solution dispensing unit 20. In dispensing the cleaning liquid Lq, the cleaning liquid Lq in any relevant probe may be directly discharged into the reaction vessel 141, or the cleaning liquid Lq in any relevant probe may be discharged into the specimen vessel 121 whose inside is empty or the reaction vessel 141 once and then a predetermined amount of the discharged cleaning liquid Lq may be absorbed via the probe and discharged into the reaction vessel 141, similarly to a normal specimen.

The processing at step S1 can be performed with respect to a plurality of test items different to each other, similarly to the analysis operation for the normal specimen. The dispensing operation in this case depends on each test item, and there is a case of dispensing the reagent prior to dispensing the cleaning liquid Lq and there is another case of dispensing the cleaning liquid Lq as a specimen in an interval of dispensing two kinds of reagents, for example. In addition, there is still another case of dispensing only the cleaning liquid Lq. Therefore, each of the dispensing timing and the photometry timing is controlled by the control unit 26 for each test item.

After that, the data generating unit 23 generates analysis data for each test item by using the measurement result obtained at step S1 (step S2). A processing of generating the analysis data at step S2 is performed similarly to the processing of generating the analysis data with respect to the normal specimen.

Next, the quality determining unit 24 determines the quality of the cleaning liquid Lq by comparing the analysis data generated at step S3 with given reference data (step S3). Then, the output unit 22 outputs the determination result (step S4).

Figure 4:
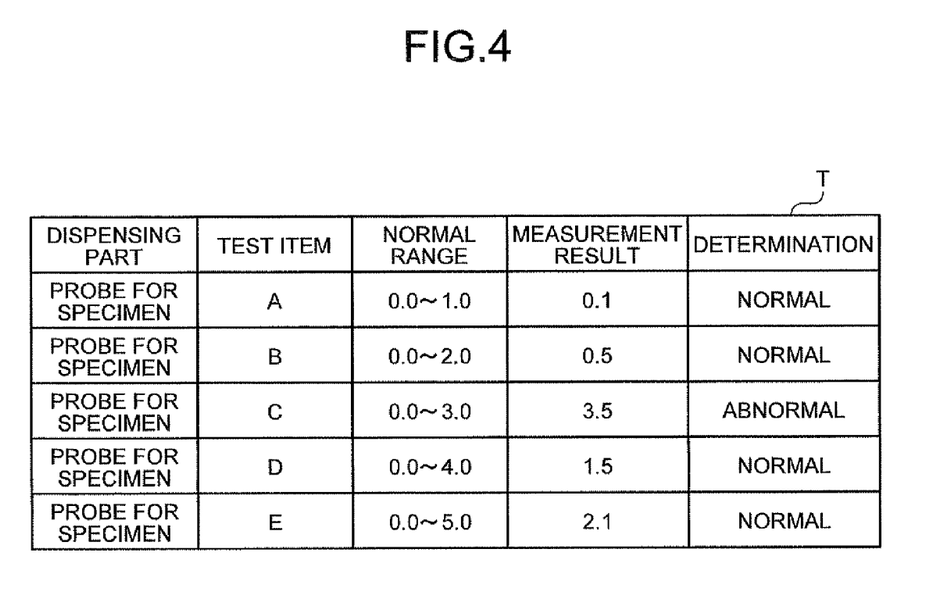
FIG. 4 shows an output example of displaying, in an output unit, a result of a quality determination of the analysis supporting liquid.

FIG. 4 shows an output example of displaying, in the output unit 22, the result of the quality determination of the cleaning liquid Lq. A table T shown in FIG. 4 shows an output example of displaying a determination result in a case of performing a quality determination of the cleaning liquid Lq filled in the probe 171 of the specimen dispensing unit 17 with respect to five kinds of test items A to E whose normal range are different from each other in the reference data. In this case, only the test item C results in being out of the normal range. Therefore, only the test item C is displayed as being "abnormal" and the other test items A, B, D, and E are displayed as being "normal".

After that, when no test item determined to be abnormal in the quality determination at step S3 is present ("No" at step S5), a series of quality control processing for the analysis supporting liquid ends. On the other hand, when a test item determined to be abnormal in the quality determination at step S3 like the test item C shown in FIG. 4 is present ("Yes" at step S5), the processing moves to the following step S6.

At step S6, it is determined whether or not to discontinue, with respect to all test items, the analysis on the normal specimen to be performed after the quality control processing for the analysis supporting liquid. When the analysis on the normal specimen is discontinued with respect to all the test items ("Yes" at step S6), the control unit 26 performs a setting for discontinueing the analysis with respect to all the test items (step S7). Due to this, the operation of the automatic analyzing apparatus 1 stops. In this case, a user is supposed to perform a maintenance including an exchange of the cleaning liquid Lq, and a cleaning of the cleaning liquid tank 177 and the tubes 31 and 32 after the operation of the automatic analyzing apparatus 1 stops.

In contrast, when the analysis on the normal specimen is not discontinued with respect to all the test items ("No" at step S6), the control unit 26 performs a setting based on a predetermined rule (step S8). As the predetermined rule here, the analysis on the normal specimen can be discontinued with respect to only the test item determined to be abnormal, for example. Besides, the analysis operation which should be performed thereafter may be set depending on the number or the kind of the test items determined to be abnormal.

More preferably if the setting is made such that the quality control method for the analysis supporting liquid in the automatic analyzing apparatus described above is automatically performed when the automatic analyzing apparatus 1 becomes a standby mode after being powered, the quality control for the analysis supporting liquid can be performed regularly.

Moreover, the setting may be made such that the quality control method for the analysis supporting liquid in the automatic analyzing apparatus described above can be performed whenever the analysis of the normal specimen has been performed predetermined number of times or for a predetermined time period, or whenever the user inputs an operation signal from the input unit 21.

When a test item determined to be abnormal is present as a result of the quality determination at step S3 ("Yes" at step S5), the output unit 22 may output to display information including a content which encourages the user to select a subsequent operation of the automatic analyzing apparatus 1. In this case, the automatic analyzing apparatus 1 is supposed to perform an operation according to the content input by the user from the input unit 21.

As described, by preparing a plurality of operation control patterns to be adopted by the automatic analyzing apparatus 1 when the quality of the cleaning liquid Lq as the analysis supporting liquid is determined to be abnormal, it becomes possible to realize a use of the automatic analyzing apparatus 1 whose reliability in analysis data is secured and an analysis efficiency is further taken into consideration.

According to the embodiment of the present invention described above, since the analysis supporting liquid which supports an analysis of a specimen is dispensed into the reaction vessel by using the specimen dispensing unit which dispenses a specimen, the reagent dispensing unit which dispenses a reagent, the cleaning unit which cleans the reaction vessel, or the diluted solution dispensing unit which dispenses a diluted solution, an optical measurement is performed with respect to the liquid including the dispensed analysis supporting liquid in the reaction vessel, analysis data of the analysis supporting liquid is generated by using the measured result, and the quality of the analysis supporting liquid is determined by comparing the generated analysis data with reference data, it is possible to accurately determine the quality of the analysis supporting liquid, after being supplied to the automatic analyzing apparatus, which supports an analysis in the automatic analyzing apparatus and to properly maintain the accuracy of the analysis.

Besides, according to the embodiment, since whether the quality, in an ultimate state just before being used, of the analysis supporting liquid used in the automatic analyzing apparatus affects analysis data or not is measured as analysis data, and when an abnormality is present, an operation control and a notification of the abnormality to the user are performed according to the abnormality, it is possible to prevent performing an analysis with the state having the abnormality in the quality of the analysis supporting liquid left as it is, and prevent an occurrence of an abnormality in analysis data. As a result of this, it is possible to eliminate a waste of an effort and a time conventionally spent until a cause of the abnormality in the analysis data is specified as lying in a deterioration of the analysis supporting liquid after the occurrence of the abnormality in the analysis data, and to realize more efficient analysis.

Furthermore, according to the embodiment, since the measurement result with respect to the analysis supporting liquid is obtained as analysis data, it becomes possible to clearly determine a degree of the influence on the analysis on the normal specimen.

In addition, according to the embodiment, since there is no necessity of adding a new component to the conventional automatic analyzing apparatus and the measurement itself concerning the quality control is the same as the analysis operation for the normal specimen, it is possible to easily control the quality of the analysis supporting liquid in the automatic analyzing apparatus.

The exemplary embodiments of the present invention have been described so far, however, the present invention should not be limited only by the specific embodiment described above.

The prevent invention can be applied to an automatic analyzing apparatus which performs an immunological analysis on ingredients of a specimen. For example, in performing an immunological analysis on a specimen by utilizing a heterogeneous reaction based on an antigen-antibody reaction, a buffering solution such as a physiological saline for performing a B/F cleaning is used. Therefore, when the present invention is applied to the automatic analyzing apparatus used for the immunological analysis using the heterogeneous reaction, the quality control processing may be performed by using purified water before generating the buffering solution as the analysis supporting liquid, or the quality control processing may be performed by using the buffering solution itself as the analysis supporting liquid. The automatic analyzing apparatus in this case requires a B/F cleaning unit which performs the B/F cleaning and a photomultiplier tube which, as the photometric unit, counts an amount of luminescence of a light emitting substance. Except for these points, the structure of this automatic analyzing apparatus is almost the same as that of the automatic analyzing apparatus described above.

As one example of cases of performing the immunological analysis, a case of using an enzyme called alkali phosphatase (ALP) as a labeled substance to perform a test for the HBsAg infection will be explained below. In the test for the HBsAg infection, a cutoff value (included in the reference data) as a boundary value for determining between positive and negative is set to 3800 counts. Since the ALP is not contained in purified water used in generating the buffering solution essentially, a counted value which provides an amount of luminescence at a time of adding a luminescent reagent into the ALP is about 300 in normal cases (the numeric value here is just shown as one example in the test for the HBsAg infection).

However, the ALP is present a lot in the natural world and can easily adhere to a hand of human beings. For this reason, there is a possibility that the purified water is polluted due to the ALP adhering to the human hand. In such a case, the value counted after the luminescent reagent is added into the polluted purified water can possibly increase up to about several thousands of counts. Therefore, once the purified water is polluted by the ALP present in the natural world, there arises a possibility that the analysis data shows an excess of the cutoff value and causes a wrong determination that the specimen which is supposed to be essentially negative.

As explained, even when an amount of a pollutant from the outside is small, an influence thereof on a measurement value can be significant and reach, in certain instances, a level of causing a wrong determination since a small amount of ingredient is measured with high sensitivity in the immunological analysis.

According to the present invention, even in the case where a high-sensitive measurement is requested like the immunological analysis described above, an abnormality in the quality of an analysis supporting liquid such as purified water can be accurately detected, and thereby a wrong determination of analysis data can be prevented and an accuracy of the analysis can be properly maintained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A quality control method for an analysis supporting liquid in an automatic analyzing apparatus which includes, to perform an analysis on a specimen, a specimen dispensing unit which dispenses the specimen by using, as a pressure transmitting medium, an analysis supporting liquid including purified water and serving to support the analysis on the specimen, a reagent dispensing unit which dispenses a reagent by using the analysis supporting liquid as the pressure transmitting medium, a cleaning unit which cleans, by using the analysis supporting liquid as a cleaning liquid, a reaction vessel in which the specimen and the reagent are mixed and made to react to each other, and a diluted solution dispensing unit which dispenses a diluted solution including the analysis supporting liquid, and which controls a quality of the analysis supporting liquid, the quality control method for the analysis supporting liquid comprising:
dispensing the analysis supporting liquid into the reaction vessel by one of the specimen dispensing unit, the reagent dispensing unit, the cleaning unit, and the diluted solution dispensing unit;
performing an optical measurement with respect to a liquid, including the analysis supporting liquid dispensed in the dispensing, in the reaction vessel, wherein the optical measurement is performed prior to any reaction using said liquid including said analysis supporting liquid;
generating analysis data of the analysis supporting liquid by using a result measured from the optical measurement; and
determining whether the quality of the analysis supporting liquid is outside a predetermined range by comparing the analysis data generated in the data generating with reference data,
wherein when it is determined that the quality is outside the predetermined range, adjusting a setting of the automatic analyzing apparatus for analyzing the specimen, said adjusting based on a predetermined rule reflective of quality control requirements for the analysis supporting liquid.

2. The quality control method for the analysis supporting liquid in the automatic analyzing apparatus according to claim 1, wherein the liquid in the reaction vessel before being subject to the optical measurement is a liquid mixture of the analysis supporting liquid and a reagent corresponding to a test item.

3. The quality control method for the analysis supporting liquid in the automatic analyzing apparatus according to claim 1, further comprising outputting information including a determination result determined in the step of determining the quality of the analysis supporting liquid.

4. The method of claim 1 wherein the analysis supporting liquid comprises ion exchanged water.

5. An automatic analyzing apparatus, comprising:
- a specimen dispensing unit which dispenses a specimen by using, as a pressure transmitting medium, an analysis supporting liquid including purified water and serving to support an analysis on the specimen;
- a reagent dispensing unit which dispenses a reagent by using the analysis supporting liquid as the pressure transmitting medium;
- a cleaning unit which cleans, by using the analysis supporting liquid as a cleaning liquid, a reaction vessel in which the specimen and the reagent are mixed and made to react to each other;
- a diluted solution dispensing unit which dispenses a diluted solution including the analysis supporting liquid;
- a photometric unit which performs an optical measurement with respect to a liquid including the analysis supporting liquid dispensed into the reaction vessel by one of the specimen dispensing unit, the reagent dispensing unit, the cleaning unit, and the diluted solution dispensing unit, wherein the optical measurement is performed prior to any reaction using said liquid including said analysis supporting liquid;
- a data generating unit which uses a result measured by the photometric unit to generate analysis data of the analysis supporting liquid;
- a quality determining unit which compares the analysis data generated by the data generating unit with reference data to determine whether a quality of the analysis supporting liquid is outside a predetermined range, and
- a control unit, which when it is determined by the quality determining unit that the quality is outside the predetermined range, adjusts a setting of the automatic analyzing apparatus for analyzing the specimen, said adjusting based on a predetermined rule reflective of quality control requirements for the analysis supporting liquid.

6. The automatic analyzing apparatus according to claim 5, wherein the liquid in the reaction vessel before being subject to the optical measurement performed by the photometric unit is a liquid mixture of the analysis supporting liquid and a reagent corresponding to a test item.

7. The automatic analyzing apparatus according to claim 5, further comprising an output unit which outputs information including a result determined by the quality determining unit.

* * * * *